US009364813B2

(12) United States Patent
Jing

(10) Patent No.: US 9,364,813 B2
(45) Date of Patent: Jun. 14, 2016

(54) SOOT GENERATOR

(71) Applicant: Lianpeng Jing, Zollikofen (CH)

(72) Inventor: Lianpeng Jing, Zollikofen (CH)

(*) Notice: Subject to any disclaimer, the term of this patent is extended or adjusted under 35 U.S.C. 154(b) by 0 days.

(21) Appl. No.: 14/732,586

(22) Filed: Jun. 5, 2015

(65) Prior Publication Data
US 2015/0283533 A1 Oct. 8, 2015

Related U.S. Application Data

(63) Continuation of application No. PCT/CH2013/000204, filed on Nov. 29, 2013.

(30) Foreign Application Priority Data

Dec. 7, 2012 (CH) ...................................... 2735/12

(51) Int. Cl.
| G01N 31/00 | (2006.01) |
| B01J 19/24 | (2006.01) |
| C09C 1/50 | (2006.01) |
| F23D 5/04 | (2006.01) |
| F23D 5/18 | (2006.01) |
| F23D 11/44 | (2006.01) |
| G01N 33/00 | (2006.01) |

(52) U.S. Cl.
CPC . *B01J 19/24* (2013.01); *C09C 1/50* (2013.01); *F23D 5/045* (2013.01); *F23D 5/18* (2013.01); *F23D 11/446* (2013.01); *G01N 33/0006* (2013.01); *B01J 2219/00087* (2013.01); *B01J 2219/24* (2013.01); *F23D 2209/00* (2013.01); *F23D 2900/21007* (2013.01)

(58) Field of Classification Search
CPC .................................. F01N 1/00; G01N 31/00
See application file for complete search history.

(56) References Cited

FOREIGN PATENT DOCUMENTS

| CN | 1353803 A | 6/2002 |
| DE | 28 42 977 A1 | 4/1980 |
| EP | 1 055 877 A1 | 11/2000 |
| EP | 1 055 877 B1 | 9/2003 |
| EP | 1 590 408 B1 | 12/2006 |
| JP | 409210323 A * | 8/1997 |
| WO | WO 2010/006723 A2 | 1/2010 |

OTHER PUBLICATIONS

Dr. Lutz v. Meyerinck, "Druckkocher: Funktion, Aufbau, Betrieb und Reparatur" Ohlson 38, Nov. 2011, pp. 1-24, XP002693940, Retrieved from the Internet: URL:http://www.ohlson38.de/Ohlson38%20Documnets/Ohlson38%20Manuals/files/petroleum.V207.pdf.
International Search Report of corresponding International PCT Application No. PCT/CH2013/000204, dated May 3, 2014.
Chinese First Examination Report of corresponding China Application No. 201380063703.2, dated on Mar. 4, 2016.

* cited by examiner

*Primary Examiner* — Jyoti Nagpaul
(74) *Attorney, Agent, or Firm* — J.C. Patents

(57) ABSTRACT

The soot generator comprises a combustion chamber (11), in which fuel (16) can be burnt with an oxidizing agent (21) in at least one soot particle-producing flame (33), a fuel feed line (15) for supplying fuel (16) to the combustion chamber (11), a soot removal line (36), which is connected to the combustion chamber (11), into which soot removal line quenching gas (38) can be conducted and out of which soot particles can be transported, and a heating device (25-31) for heating the fuel feed line (15) at at least one heating location (15a).

14 Claims, 1 Drawing Sheet

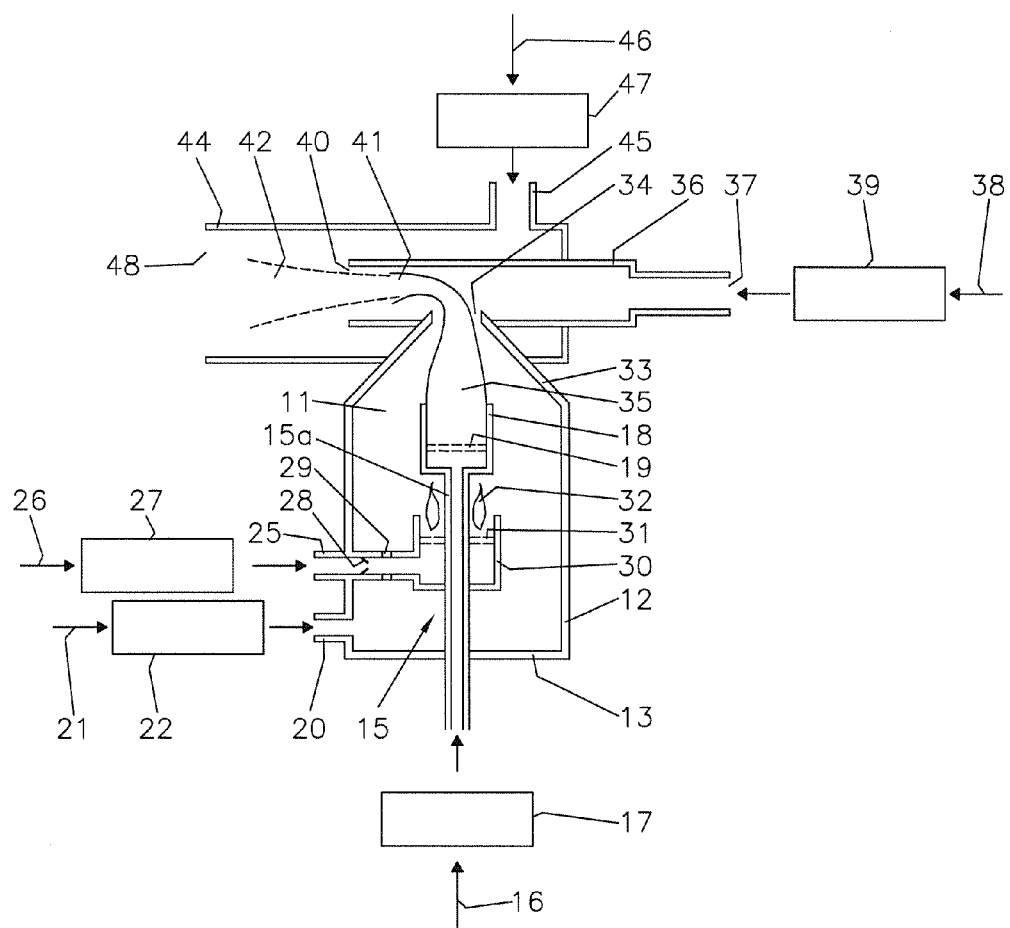

SOOT GENERATOR

CROSS-REFERENCE TO RELATED APPLICATIONS

This application is a continuation of International Application No. PCT/CH2013/000204, filed on Nov. 29, 2013, which claims the priority benefit of Switzerland Patent Application No. 2735/12, filed on Dec. 7, 2012. The contents of the above identified applications are incorporated herein by reference in their entireties.

FIELD OF THE TECHNOLOGY

The invention relates to a soot generator according to the preamble of claim 1.

BACKGROUND

The patents EP 1 055 877 B1 and EP 1 590 408 B1 by the same applicant describe soot generators that are capable of generating soot particles having well-defined chemical and physical properties. To this end, fuel and oxidizing gas are fed into a combustion chamber in such a way as to form a diffusion flame, which creates soot particles. The tip of the diffusion flame is exposed to the oncoming flow of a quenching gas, so that the combustion process is stopped and the soot particles are carried away. These soot generators have proven to be particularly successful when used with gaseous fuels. It has been found that liquid fuels are less suitable for generating soot particles having the desired properties.

SUMMARY

One object of the present invention is therefore to improve upon the known soot generators, so that when using liquid fuel in particular, soot particles with the most well-defined possible properties can be produced.

A soot generator according to the invention, which solves this problem, is defined in claim 1. In the additional claims, preferred embodiments as well as a use of the soot generator are described.

According to claim 1, the soot generator according to the invention comprises a heating device for heating the fuel feed line at at least one heating location. This makes it possible to heat liquid fuel before its actual combustion, so that it evaporates at least partially. This improves combustion and thus facilitates the production of soot particles having well-defined properties.

BRIEF DESCRIPTION OF THE DRAWINGS

The invention is explained below on the basis of one exemplary embodiment, with reference to:

FIG. 1, which shows schematically a soot generator according to the invention in cross section.

DETAILED DESCRIPTION

The soot generator illustrated in FIG. 1 comprises a combustion chamber 11, which is bordered at the side by an exterior wall 12. The exterior wall 12, which is designed to be cylindrical, for example, has a bottom 13, through which a feed line in the form of an interior pipe 15 passes. This has a cylindrical shape, for example, and is preferably arranged coaxially with the exterior wall 12.

The inlet of the inside tube 15 can be connected to a fuel tank (not shown) for supplying fuel 16. To regulate the flow rate (liter per second) a suitable adjusting device 17, for example a flow regulator or a metering pump, is provided between the fuel tank and the inlet of the interior pipe 15. Liquid fuel, for example diesel fuel, gasoline, kerosene, hexane, etc., is stored in the fuel tank.

The inside tube 15 opens into an outlet 18. The latter is designed to be open at the top and is formed by an enlargement in the pipe cross section. The cross section of the opening of the outlet 18 is thus larger than the cross section of the end 15a of the interior pipe 15. The outlet 18 is formed, for example, by a cylindrical pipe section having a bottom in which the inlet of the interior pipe 15 is situated. The outlet 18, which is shown in the form of steps in FIG. 1, may also have a different shape, for example, it may be in the form of a continuous enlargement, which is stepless on the interior surface and on the exterior surface. An aperture 19 with through-openings is optionally arranged in the outlet 18.

At its lower end according to FIG. 1, a second feed line 20 opens in the exterior wall 12, through which oxidizing agent 21 can be passed into the combustion chamber 11. The second feed line 20 can be connected via a flow regulator 22 for regulating the flow rate to a container (not shown), in which the oxidizing agent 21 is stored. For example, compressed air, synthetic air (80% nitrogen gas, 20% oxygen gas) or other oxidizing gases are conceivable as the oxidizing agent 21.

In addition, the soot generator has a heating device 25-31, which is described in greater detail below and which serves to heat the first feed line 15 at at least one location 15a. A third feed line 25 for supplying fuel 26 passes through the exterior wall 12 and opens into a preheating burner 30. The third feed line 25 can be connected via a flow regulator 27 for regulating the flow rate to a container (not shown), in which the fuel 26 is stored. This fuel is preferably a combustible gas, for example a gas containing hydrocarbon such as propane.

The section of the third feed line 25, which runs inside of the exterior wall 12, is provided with one or more inlet openings 29. During operation, oxidizing agent 21, which is fed into the combustion chamber 11 through the second feed line 20, passes through these openings into the third feed line 25, where it is mixed with the fuel 26. To facilitate the intake of oxidizing agent 21, the third feed line 25 has a constriction 28, for example a nozzle, upstream from the inlet openings 29, so that the Venturi effect can be utilized. In this process, the fuel 26, which flows more rapidly during operation because of the constriction 28, creates an underpressure, so that oxidizing agent 21 is drawn in through the inlet openings 29 and becomes mixed with the fuel 26.

The preheating burner 30 runs around the interior pipe 15 and is designed here to be open at the outlet end. An aperture 31 with through-openings is optionally arranged in the preheating burner 30. The end 15a of the interior pipe 15, which runs through the preheating burner 30, forms a heating location at which the fuel 16 in the interior pipe 15 can be heated. The preheating burner 30 is not absolutely necessary for creating a heating location. It is also possible to omit it, so that a flame can be generated at the outlet of the feed line 25, this flame being directed across the feed line 15.

At least the part 15a of the interior pipe 15 to be heated is manufactured from a thermally conductive material, so that the heat generated on the exterior wall can be carried into the interior of the interior pipe 15.

The part of the soot generator, which serves to actually produce and remove the soot particles, will be explained below.

On the outlet end, the combustion chamber 11 has a wall 33, which tapers as seen in the direction of flow and is provided at the end with an opening 34, which is arranged in a soot removal line 36. At the inlet end, this comprises an inlet 37 for supplying quenching gas 38, which is stored in a quenching tank (not shown) in the form of a gas bottle, for example. To regulate the flow rate of the quenching gas 38 into the soot removal line 36, a flow regulator 39 is mounted between the quenching gas tank and the inlet 39.

At the other end of the soot removal line 36, there is an outlet 40 out of which, among others, the quenching gas can flow together with the soot particles. The soot removal line 36 is formed by a pipe or a plurality of pipe segments joined together, for example.

At least one ignition means (not shown), which, for example, is configured to generate ignition sparks, is preferably provided in the combustion chamber 11 for ignition of the fuel 16 and/or of the combustible gas 26.

The soot generator is operated as described below:

First, in a preheating burner 30 or—if that is omitted—at the outlet end of the feed line 25, a flame 32 for heating the first feed line 15 is created by introducing combustible gas 26 into the third feed line 25, where it is mixed with oxidizing agent 21 and is finally ignited. If the aperture 31 is provided, then it is possible to keep the flow conditions as laminar as possible and therefore to create a particularly smooth-burning flame 32. This flame heats the first feed line 15 at the heating location 15a. If liquid fuel 16 is then introduced into the feed line 15, the fuel evaporates at the heating location 15a and, primarily in gaseous form, then enters the outlet 18, where it is finally ignited. The ignition may be accomplished easily, for example, by directing more combustible gas 26 to the preheating burner 30 briefly so that the growing flame 32 extends as far as the opening to the outlet 18 on the outlet end, where it ignites the fuel 16 flowing out.

After the ignition, a diffusion flame 15 develops over the opening of the outlet 18. Thereby, the fuel 16 flowing out is surrounded by the oxidizing agent 21, which is fed in through the feed line 20, in an essentially parallel flow. The flow conditions in the fuel 16 flowing out can be kept laminar to an improved extent by the provision of the aperture 19 in the outlet 18. Then an essentially cylindrical diffusion flame 35 develops, in which soot particles are formed due to the combustion of the fuel 16 with the oxidizing agent 21.

Depending on the intended purpose of the soot particles, however, it is also conceivable to design the soot generator for producing soot particles, so that a turbulent flame develops above the outlet 18.

To obtain the soot particles, quenching gas 38 is passed through the soot removal line 36, so that the gas becomes mixed with the substance flow which emerges from the combustion chamber and contains the soot particles, among others, and the combustion processes at the quenching location 41 are thereby stopped. The soot particles are then carried away by the quenching gas flow to the outlet 40.

An inert gas such as nitrogen gas, noble gas or carbon dioxide may be used as the quenching gas. It is also conceivable to use air as the quenching gas, in particular air that is cooler than the flame 35. For example, air from the environment can be sent by means of a pump through the soot removal line 36. Since the temperature of the air corresponds approximately to the room temperature and is therefore lower than the flame temperature, the combustion processes at the extinguishing location 41 are thereby stopped due to cooling. This process can be supported by a relatively high velocity of flow of the air in the soot removal line 36 so that the end of the flame 35 protruding out of the opening 34 is practically blown out.

The soot generator optionally has dilution means 44-48. For this purpose, a jacketed pipe 44 in which the outlet 40 of the soot removal line 36 is arranged and which is designed to be a cylinder, for example, is provided. Upstream from the outlet 40, there is a connection 45 for feeding a diluting gas 46 (for example, air) into the jacketed pipe 44. The open end 48 of the jacketed pipe 44 is located downstream from the outlet 40.

During operation, the diluting gas 46 flows into the jacketed pipe 44, where it is mixed with the quenched substance flow 42 emerging from the outlet 40, thereby diluting the substance flow. As an alternative to using a jacketed pipe 44, it is also conceivable to provide openings at one end of the soot removal line 36, for example, two openings, which are arranged symmetrically, through which the diluent gas 46 can be conducted to the substance flow 42.

The inflow rate of the diluent gas 46 is adjustable by providing a flow regulator 47, so that the concentration of soot particles (number of particles per $m^3$), which finally flows out of the open end of the soot generator, can be varied.

The soot generator described here is suitable in particular for production of soot particles from a liquid fuel. Depending on the intended application, however, it is also possible to use a gaseous fuel to produce the flame 35. In this case the preheating flame 32 is used only temporarily if at all, for example, for ignition of the flame 35. This soot generator can thus be used optionally with liquid or gaseous fuel.

Soot particles with an essentially reproducible size distribution and with a defined chemical composition can be produced with this soot generator.

Various parameters, such as size and concentration as well as chemical composition, influence the soot particle properties:

- type and composition of the fuel
- inflow rate (in l/sec) of the fuel
- inflow rate of the oxidizing agent
- inflow rate of the quenching gas
- quenching location of the diffusion flame due to quenching gas (determined essentially by the distance between the opening of the outlet 18 and the mouth 34 of the combustion chamber 11)
- etc.

Depending on the choice of the parameters, for example, soot particles whose size has an essentially Gaussian distribution on a logarithmic scale can be produced, where the maximum is smaller than 1 micrometer, for example, in the range of 0.01 to 0.3 micrometer. However, it is also possible to produce soot particles larger than 1 micrometer through appropriate choice of the fuel and/or the design of the soot removal line.

The soot generator can be used in a variety of ways, for example, for calibration of soot particle measuring devices, for exhaust gas measurement in motor vehicles, for testing filters, for analyzing aerosols, for testing smoke alarms, for producing soot samples and reference material, etc.

From the preceding description, numerous modifications will be accessible to those skilled in the art without going beyond the scope of protection of the invention, which is defined by the claims.

It is thus possible, for example, to design the soot generator so that the feed line 15 can be heated outside of the combustion chamber 11. To do so, for example, the preheating burner 30—if one is present—and the feed line 25 are arranged on the other side of the bottom 13.

The openings 28 in the third feed line 25 may also be arranged outside of the combustion chamber 11 in order to draw in the oxidizing agent, which may also be ambient air.

In addition, it is conceivable to design the heating device 25-31, so that the feed line 15 can be heated at several locations.

It is also possible to design the heating device, so that, instead of a premixed flame, a different type of flame, for example, a diffusion flame can also be produced in the preheating burner 30. If premixing of the oxidizing agent is not provided, then the openings 28 and the constriction 29 may be omitted.

In addition, the heating device may also be designed so that the feed line 15 can be heated electrically, in that one or more electric heating elements are provided.

As another embodiment, the soot generator can also be designed so that the same fuel is used to form the flames 32 and 33. Since the flame 32 is needed only for preheating the feed line 15, optimum combustion is not absolutely necessary here. It is therefore possible to also use liquid fuel to form the two flames 32 and 33.

The combustion chamber 11 with the outlet 34 need not necessarily be arranged across the soot removal line 36, as shown in FIG. 1. It is conceivable to design the upper end 33 of the exterior wall 12, so that it is curved to allow the middle part of the flame 33 to be deflected accordingly. Depending on the intended application, the angle by which the upper end 33 is curved can be selected to be from 0 to 90 degrees.

In addition, it is conceivable to provide a constriction in the soot removal line in order to create an underpressure in the opening 34, based on the Venturi effect, and thereby draw in oxidizing agent as described in the patent EP 1 590 408 B1. In a particularly simple embodiment, this underpressure may be utilized to intake ambient air as an oxidizing agent through an opening that passes through an opening in the combustion chamber 11 extending through to the outside. In this case, the gas bottle with the oxidizing agent 21 stored in it as well as the feed line 20 and the flow regulator 22 can be omitted.

The soot generator may also be designed so that several flames, which produce soot particles, are provided.

What is claimed is:

1. Soot generator, comprising
   a combustion chamber (11), in which fuel (16) can be burnt with an oxidizing agent (21) in at least one flame (33) that produces soot particles,
   a fuel feed line (15) for supplying fuel (16) to the combustion chamber (11) and
   a soot removal line (36), which is connected to the combustion chamber (11) and into which quenching gas (38) can be conducted and out of which soot particles can be removed, wherein the soot generator further comprises
   a heating device (25-31) comprising an additional fuel feed line (25) and a preheating burner (30) connected to additional fuel feed line (25) and located in the combustion chamber (11), wherein the preheating burner (30) is used for heating the fuel feed line (15) at at least one heating location (15a) in the combustion chamber (11).

2. Soot generator according to claim 1, wherein the preheating burner (30) is used for creating a heating flame (32) and runs around the fuel feed line (15) or transversely thereto.

3. Soot generator according to claim 2, wherein the preheating burner has an outlet in which an aperture (31) having through-openings is situated.

4. Soot generator according to claim 1, wherein the additional fuel feed line (25) is used for supplying fuel (26), which is different from the fuel (16) in the first fuel feed line (15) and/or which is a combustible gas.

5. Soot generator according to claim 4, wherein the additional fuel feed line (25) has at least one opening (29) through which oxidizing agent (21) can be supplied for mixing with the fuel (26) directed into the additional fuel feed line (25).

6. Soot generator according to claim 5, wherein a construction (28) is provided in the additional fuel feed line (25) upstream from the at least one opening (29).

7. Soot generator according to claim 4, wherein at least one igniting means is arranged in the fuel chamber (11).

8. Soot generator according to claim 7, wherein the first fuel feed line (15) opens into an outlet (18), which has a widened shape and/or in which an aperture (19) with through-openings is arranged.

9. Soot generator according to claim 8, wherein the fuel chamber (11) is arranged transversely to the soot removal line (36), so that the flame (33) can be exposed transversely to an oncoming flow of quenching gas.

10. Soot generator according to claim 9, which has a diluting device (44-48) for diluting the concentration of the soot particles discharged out of the soot removal line (36).

11. Use of a soot generator according to claim 1, for producing soot particles, which can be used in particular as a soot sample and/or as a reference material and/or for calibrating measurement devices, for testing sensors and/or for testing filters.

12. Soot generator according to claim 1, wherein the quenching gas is an inert gas.

13. Soot generator according to claim 1, wherein the fuel (16) supplied into the first fuel feed line (15) is a liquid fuel.

14. Soot generator, comprising
   a combustion chamber (11), in which fuel (16) can be burnt with an oxidizing agent (21) in at least one flame (33) that produces soot particles,
   a fuel feed line (15) for supplying fuel (16) to the combustion chamber (11) and
   a soot removal line (36), which is connected to the combustion chamber (11) and into which quenching gas (38) can be conducted and out of which soot particles can be removed, wherein the soot generator further comprises
   a heating device (25-31) comprising an additional fuel feed line (25) and a preheating burner (30) connected to additional fuel feed line (25) and located below the combustion chamber (11), wherein the preheating burner (30) is used for heating the fuel feed line (15) at at least one heating location (15a) below the combustion chamber (11).

* * * * *